United States Patent [19]

Abe et al.

[11] Patent Number: 5,250,729

[45] Date of Patent: Oct. 5, 1993

[54] PROCESS FOR PREPARING UNSATURATED CARBOXYLIC ACID OR ESTER THEREOF

[75] Inventors: Takafumi Abe; Shinichi Hieda, both of Niigata, Japan

[73] Assignee: Mitsubishi Gas Chemical Company, Inc., Tokyo, Japan

[21] Appl. No.: 445,543

[22] Filed: Dec. 4, 1989

[30] Foreign Application Priority Data

Jan. 26, 1989 [JP] Japan .................................. 1-15110

[51] Int. Cl.$^5$ ...................... C07C 57/00; C07C 51/00; C07C 67/00; C07C 69/00
[52] U.S. Cl. .................................. 562/599; 560/212
[58] Field of Search .................. 562/599; 560/212

[56] References Cited

U.S. PATENT DOCUMENTS 3,657,331  4/1972  Ackermann et al. .......... 260/526 N
3,980,670  9/1976  Kummer et al. ............... 260/343.6

FOREIGN PATENT DOCUMENTS 44-20611   9/1969  Japan .
44-20612   9/1969  Japan .
45-15724   6/1970  Japan .
149239     9/1982  Japan ................... 562/599
60-184047  9/1985  Japan .
584607     1/1948  United Kingdom .

*Primary Examiner*—Arthur C. Prescott
*Attorney, Agent, or Firm*—Frishauf, Holtz, Goodman & Woodward

[57] ABSTRACT

A process for preparing an $\alpha, \beta$-unsaturated carboxylic acid and/or an $\alpha, \beta$-unsaturated carboxylic acid ester from at least one ester selected from $\alpha$-hydroxycarboxylic acid ester, $\alpha$-alkoxycarboxylic acid ester and $\beta$-alkoxycarboxylic acid ester as a starting material by a vapor-phase catalytic reaction in the presence of a crystalline aluminosilicate as a catalyst.

According to the process, $\alpha, \beta$-unsaturated carboxylic acid and/or an ester thereof can be produced in a mild condition and a high yield.

2 Claims, No Drawings

PROCESS FOR PREPARING UNSATURATED CARBOXYLIC ACID OR ESTER THEREOF

BACKGROUND OF THE INVENTION

1. Field of the invention

This invention relates to a process for preparing industrially an α, β-unsaturated carboxylic acid or an ester thereof by using at least one ester selected from an α-hydroxycarboxylic acid ester, an α-alkoxycarboxylic acid ester and δ-alkoxycarboxylic acid ester as a starting material.

The α,β-unsaturated carboxylic acid ester and the α,β-unsaturated carboxylic acid are widely available in industry as starting materials for producing synthetic resins and reactive monomers, respectively. In particular, methyl methacrylate and methacrylic acid obtained from methyl α-hydroxyisobutyrate and/or methyl α- or β-methoxyisobutyrate have been industrially important because methyl methacrylate can be used as a starting material for polymethyl methacrylate having excellent weather resistance and transparency and because methacrylic acid can be used as a starting material for various methacrylates.

2. Description of the Related Arts

As for a process of preparing α, β-unsaturated carboxylic acid and/or an ester thereof, a process in which a dehydrating reaction of an α-hydroxycarboxylic acid ester is carried out in a liquid phase, has heretofore been described in, for example, U.S. Pat. No. 3,487,101.

In addition, in Japanese Patent Application Laid-Open No. 184047/1985, a process is disclosed in which methyl methacrylate is prepared by reacting 90 to 100% concentrated sulfuric acid and methyl α-hydroxyisobutyrate in a liquid phase.

However, in the process for preparing methacrylic acid esters using sulfuric acid, there are great difficulties in their practical application on an industrial scale, because an extremely excess amount of high concentration sulfuric acid is required and the problem of processing a large amount of waste sulfuric acid diluted with water formed by the reaction is involved.

On the other hand, a process has been proposed for preparing methyl methacrylate from methyl α-hydroxyisobutyrate by a vapor phase catalytic reaction using a solid catalyst such as phosphate.

For example, in Japanese Patent Publications No. 0611/1969, No. 20612/1969 and No. 15724/1970, there are disclosed processes in which high boiling point materials, such as methyl α-hydroxyisobutyrate, methyl α-methoxyisobutyrate and methyl β-methoxyisobutyrate, among the impurities contained in crude methyl methacrylate synthesized by the acetone cyanohydrin method, are passed through a catalytic layer, wherein solid phosphoric acid, alkali metal salts of phosphoric acid, or alkaline earth metal salts of phosphoric acid deposited on silica or silica-alumina to obtain methyl methacrylate and methacrylic acid.

However, when these phosphate-based catalysts are used, a high reaction temperature is required, so that deposition of a large amount of carbonaceous material and a side reaction, such as a hydrogenation reaction occur, causing problems in that, for example, methyl isobutyrate is formed as a by-product in large quantities, and therefore the above described processes are not satisfactory for practical use.

SUMMARY OF THE INVENTION

The present inventors have intensively studied the problems involved in the prior art. Accordingly, an object of the present invention is to provide an industrial process for preparing α, β-unsaturated carboxylic acid and/or an ester thereof in more moderate conditions and high yield.

The present inventors have found that the process of using a crystalline aluminosilicate as a catalyst is the best process for solving the various disadvantages in the prior art and have accomplished the present invention. That is, the present invention provides a process for preparing an α, β-unsaturated carboxylic acid and/or an α,β-unsaturated carboxylic acid ester, which comprises reacting at least one ester selected from α-hydroxycarboxylic acid ester, α-alkoxycarboxylic acid ester and β-alkoxycarboxylic acid ester in a vapor phase in the presence of a crystalline aluminosilicate.

DESCRIPTION OF THE PREFERRED EMBODIMENTS

In the following, the process of the present invention is described in more detail.

We, the present inventors, have intensively studied the process for synthesizing α, β-unsaturated carboxylic acid and/or an ester thereof by using one or more esters selected from α-hydroxycarboxylic acid ester, α-alkoxycarboxylic acid ester and β-alkoxycaboxylic acid ester as a starting material. At first, we carried out investigations of various amorphous silica and silica-alumina, etc., which are typical dehydrating catalysts. However, it has been found that these catalysts seldom show conversion activities to α-hydroxycarboxylic acid ester, α-alkoxycarboxylic acid ester and/or β-alkoxy-carboxylic acid ester, or rather promote decomposition reactions thereof, so that the objective product of dehydration reactions cannot be obtained.

Thus, we have carried out various investigations using a crystalline aluminosilicate catalyst and found that, surprisingly, the α, β-unsaturated carboxylic acid and/or an ester thereof can be obtained with a high yield when X type or Y type zeolite is used as a catalyst.

The X-type and the Y-type zeolites mentioned herein are synthetic zeolites, and for example, when it is the NaX type or the NaY type zeolite, it is represented by the following formula: NaX type:

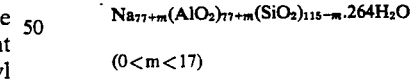

$(0 < m < 17)$

NaY type:

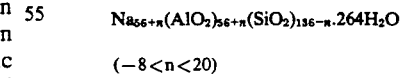

$(-8 < n < 20)$

These zeolites, include commercially available zeolites such as Molecular sieve 13X (trade mark).

Furthermore, the α-hydroxycarboxylic acid ester, α-alkoxycarboxylic acid ester and/or β-alkoxycarboxylic acid ester can be reacted by diluting it in various solvents, whereby the α, β-unsaturated carboxylic acid and/or an ester thereof can be obtained with high selectivity.

When an alcohol which corresponds to an alkoxy portion of the ester is used as a diluent, the selectivity of the α, β-unsaturated carboxylic acid ester can be increased. When water is used as a diluent, the selectivity of the α, β-unsaturated carboxylic acid can be increased.

In particular, in the process of the present invention, when methyl α-hydroxyisobutyrate is used as a starting material and methanol is used as a diluent, methyl methacrylate containing substantially no impurities, such as methyl isobutyrate can be synthesized. Therefore, methyl methacrylate with a high purity can be easily obtained by a simple operation, such as extraction from the diluent or distillation in accordance with conventional methods.

Next, the process of the present invention is explained by referring to the reaction following route with the following reaction formulae in order to explain it more easily:

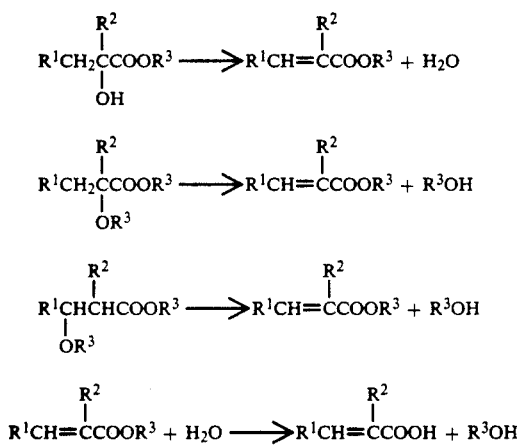

wherein $R^1$ and $R^2$ each represent a hydrogen or an alkyl group having 1 to 3 carbon atoms, and $R^3$ represents an alkyl group having 1 to 5 carbon atoms.

The process of the present invention can be performed as shown below.

That is, into a corrosion resistance tubular reactor is charged a predetermined amount of a crystalline aluminosilicate catalyst, and if necessary, a small amount of nitrogen is passed through it as a carrier gas, and at a reaction temperature in the range of 150° to 450° C., preferably 200° to 350° C., a solution of the α-hydroxycarboxylic acid ester, α-alkoxycarboxylic acid ester and/or β-alkoxycarboxylic acid ester with a concentration of 10 to 100%, preferably 30 to 85% was supplied thereto continuously as the starting material.

When a solvent is used in the reaction, an alcohol corresponding to an alkoxy portion of the ester is used to produce the α, β-unsaturated carboxylic acid ester. In addition, water is used to produce α, β-unsaturated carboxylic acid.

In the process of the present invention, the reaction can be carried out with a vapor phase catalytic reaction, but it is preferably carried out with a vapor phase reaction using a fixed bed. The liquid of the starting material is also preferably used by preliminary heating and then supplying it in a vapor state.

Furthermore, the α-hydroxycarboxylic acid ester, α-alkoxycarboxylic acid ester and β-alkoxycarboxylic acid ester as may be used singly or in a mixture as starting materials.

When the methyl α-hydroxyisobutyrate, methyl α-methoxybutyrate and/or methyl β-methoxybutyrate are used as starting materials, a small amount of unreacted starting material or by-product such as acetone is contained in a reaction product, in addition to the objective methyl methacrylate and methacrylic acid.

When an extraction method or a distillation method is applied to the reaction product, a product of methyl methacrylate with a high purity can be easily obtained. In addition, the unreacted starting material recovered by this operation can be utilized again in the reaction.

According to the process of the present invention, α, β-unsaturated carboxylic acid and/or an ester thereof can be prepared easily and economically with more moderate conditions and a high yield. Therefore, it has great industrial signification.

The present invention is described in greater detail with reference to the following examples, although it is not intended to be limited thereto.

EXAMPLE 1

In a tubular reactor made of a quartz having an inner diameter of 15 mm and length of 450 mm was packed 10 g of Molecular Sieve 13X (produced by Wako Junyaku K.K.) as a catalyst and the temperature of the resulting catalytic layer was maintained at 240° C.

Six g/hr. of methyl α-hydroxyisobutyrate solution with a concentration of 50% dissolved in methanol as a solvent was vaporized through a preheating layer and supplied into the catalytic layer with 3 ml/min. of nitrogen gas.

The solution produced was analyzed to obtain the results that a conversion of methyl α-hydroxyisobutyrate was 99%, a selectivity to methyl methacrylate was 93%, a selectivity to methacrylic acid was 2% and selectivities to acetone and methyl α-methoxyisobutyrate were each less than 1%.

Even in 40 hours after starting the reaction, the yield of methyl methacrylate was 90% or higher.

In addition, in 150 hours after starting the reaction at a reaction temperature of 265° C., no decrease in the conversion of methyl α-hydroxyisobutyrate was observed and the yield of methyl methacrylate was 90% or higher.

EXAMPLE 2

The reaction was carried out in the same manner as in Example 1 except for using water in place of methanol as a diluent.

The solution produced was analyzed to obtain the results that a conversion of methyl α-hydroxyisobutyrate was 99%, a selectivity to methacrylic acid was 92%, a selectivity to methyl methacrylate was 3% and selectivities to acetone and methyl α-methoxyisobutyrate were each less than 1%.

Even in 40 hours after starting the reaction, the yield of methacrylic acid was 90% or higher.

In addition, in 150 hours after starting the reaction at a reaction temperature of 265° C., no decrease in the conversion of methyl α-hydroxyisobutyrate was observed the yield of methacrylic acid was 90% or higher.

EXAMPLE 3

The reaction was carried out in the same manner as in Example 1 except for replacing methyl α-hydroxyisobutyrate with methyl β-methoxyisobutyrate as a starting material.

The solution produced was analyzed to obtain the results that a conversion of methyl β-methoxyisobutyrate was 99%, a selectivity to methyl methacrylate was 95%, selectivities to methacrylic acid and methyl α-methoxyisobutyrate were each less than 1%.

Even in 40 hours after starting the reaction, the yield of methyl methacrylate was 90% or higher.

In addition, in 150 hours after starting the reaction at a reaction temperature of 265° C., no decrease in the conversion rate of methyl β-methoxyisobutyrate was observed and the yield of methyl methacrylate was 90% or higher.

EXAMPLE 4

The reaction was carried out in the same manner as in Example 1 except for replacing methyl α-hydroxyisobutyrate with methyl lactate as a starting material.

The solution produced was analyzed to obtain the results that a conversion of methyl lactate was 99%, a selectivity to methyl acrylate was 93%, a selectivity to acrylic acid was 2% and selectivities to acetaldehyde and methyl α-methoxypropionate were each less than 1%.

Even in 40 hours after starting the reaction, the yield of methyl methacrylate was 90% or higher.

What is claimed is:

1. In a process for preparing a product comprising an α,β-unsaturated carboxylic acid, an α,β-unsaturated carboxylic acid ester or a mixture thereof from a starting material comprising at least one ester selected from the group consisting of an α-hydroxycarboxylic acid ester, an α-alkoxycarboxylic acid ester and a β-alkoxycarboxylic acid ester by a vapor-phase catalytic reaction, the improvement which comprises said catalyst being a crystalline aluminosilicate Molecular Sieve 13X zeolite, the starting material being selected from the group consisting of methyl α-hydroxyisobutyrate, methyl β-methoxyisobutyrate and methyl lactate; and the process being carried out at a temperature of 200° to 350° C.

2. The process of claim 1, wherein the zeolite has the formula $Na_{66+m}(AlO_2)_{77+m}(SiO_2)_{114-m}.264H_2O$, wherein $0<m<17$.

* * * * *